United States Patent
Vuligonda

(10) Patent No.: US 11,976,021 B2
(45) Date of Patent: May 7, 2024

(54) SYNTHESIS OF TETRAHYDRONAPHTHALENOLS AND USES THEREOF

(71) Applicant: Io Therapeutics, Inc., Spring, TX (US)

(72) Inventor: Vidyasagar Vuligonda, Spring, TX (US)

(73) Assignee: Io Therapeutics, Inc., Spring, TX (US)

(*) Notice: Subject to any disclaimer, the term of this patent is extended or adjusted under 35 U.S.C. 154(b) by 0 days.

(21) Appl. No.: 18/342,402

(22) Filed: Jun. 27, 2023

(65) Prior Publication Data

US 2023/0416190 A1 Dec. 28, 2023

Related U.S. Application Data

(60) Provisional application No. 63/355,880, filed on Jun. 27, 2022.

(51) Int. Cl.
| | |
|---|---|
| *C07C 233/66* | (2006.01) |
| *A61K 31/196* | (2006.01) |
| *C07C 231/02* | (2006.01) |
| *C07C 231/12* | (2006.01) |
| *C07C 231/24* | (2006.01) |
| *C07C 235/66* | (2006.01) |

(52) U.S. Cl.
CPC .......... *C07C 233/66* (2013.01); *A61K 31/196* (2013.01); *C07C 231/02* (2013.01); *C07C 231/12* (2013.01); *C07C 231/24* (2013.01); *C07C 235/66* (2013.01)

(58) Field of Classification Search
None
See application file for complete search history.

(56) References Cited

U.S. PATENT DOCUMENTS

| | | | |
|---|---|---|---|
| 5,675,024 A | * | 10/1997 | Teng ................. A61P 35/00 548/200 |
| 5,856,490 A | | 1/1999 | Teng et al. |
| 5,965,606 A | | 10/1999 | Teng et al. |
| 6,387,950 B2 | | 5/2002 | Nehme et al. |
| 9,907,768 B2 | | 3/2018 | Chandraratna et al. |
| 10,004,708 B2 | | 6/2018 | Chandraratna et al. |
| 10,004,709 B2 | | 6/2018 | Chandraratna et al. |
| 10,123,982 B2 | | 11/2018 | Chandraratna et al. |
| 10,213,401 B2 | | 2/2019 | Chandraratna et al. |
| 10,231,944 B2 | | 3/2019 | Chandraratna et al. |

(Continued)

FOREIGN PATENT DOCUMENTS

| | | |
|---|---|---|
| WO | WO 2017/091762 | 6/2017 |
| WO | WO 2017/214575 | 12/2017 |

(Continued)

OTHER PUBLICATIONS

Beard ("Synthesis and Biological Activity of Retinoic Acid Receptor-alpha Specific Amides" Bioorg. Med. Chem. Lett. 12 (2002), p. 3145-3148) (Year: 2002).*

(Continued)

*Primary Examiner* — Amy C Bonaparte
(74) *Attorney, Agent, or Firm* — K&L Gates LLP; Louis C. Cullman; Benjamin D. Heuberger

(57) ABSTRACT

Provided herein are compounds and synthetic methods useful for preparing tetrahydronaphthalenol derivatives, and uses of the compounds prepared.

17 Claims, 2 Drawing Sheets

(56) References Cited

U.S. PATENT DOCUMENTS

| | | | |
|---|---|---|---|
| 10,363,272 B2 | 7/2019 | Chandraratna et al. | |
| 10,471,030 B2 | 11/2019 | Chandraratna et al. | |
| 10,485,775 B2 | 11/2019 | Chandraratna et al. | |
| 10,517,843 B2 | 12/2019 | Chandraratna et al. | |
| 10,532,073 B2 | 1/2020 | Chandraratna et al. | |
| 10,532,074 B2 | 1/2020 | Chandraratna et al. | |
| 10,874,627 B2 | 12/2020 | Chandraratna et al. | |
| 10,874,628 B2 | 12/2020 | Chandraratna et al. | |
| 10,874,694 B2 | 12/2020 | Chandraratna et al. | |
| 10,881,628 B2 | 1/2021 | Chandraratna et al. | |
| 11,737,996 B2 | 8/2023 | Chandraratna et al. | |
| 11,779,558 B2 | 10/2023 | Chandraratna et al. | |
| 11,786,555 B2 | 10/2023 | Chandraratna et al. | |
| 11,793,835 B2 | 10/2023 | Sanders et al. | |
| 2019/0060362 A1* | 2/2019 | Chandraratna | A61P 35/02 |

FOREIGN PATENT DOCUMENTS

| | | |
|---|---|---|
| WO | WO 2019/014468 | 1/2019 |
| WO | WO 2019/014492 | 1/2019 |
| WO | WO 2019/046591 | 3/2019 |
| WO | WO 2023/097259 | 6/2023 |

OTHER PUBLICATIONS

Richard L. Beard, et al. "Synthesis and Biological Activity of Retinoic Acid Receptor—Specific Amides" Bioorganic & Medicinal Chemistry Letters, 12, 3145-3148 (2002).

* cited by examiner

SYNTHESIS OF TETRAHYDRONAPHTHALENOLS AND USES THEREOF

RELATED APPLICATIONS

This application claims the priority of U.S. Provisional Patent Application No. 63/355,880, filed Jun. 27, 2022, the entire content of which is incorporated herein by reference.

BACKGROUND

Compound 6, which may be referred to in the literature as AGN-195183, has been prepared in a multi-step process requiring at least 7 synthetic sequences as described by Richard L. Beard, et al. in Synthesis and Biological Activity of Retinoic Acid Receptor-Specific Amides, Bioorganic & Medicinal Chemistry Letters, 12, 3145-3148 (2002). However, synthetic processes are needed that shorten the synthetic burden, improve overall yield efficiency, and provide commercial scalability. Compound 6 is useful as a modulator of retinoic acid receptor alpha (RARα), including by activation of RARα, and thereby useful in treating diseases, including RARα-related diseases.

Thus, provided herein are improved compounds and synthetic methods useful in preparing tetrahydronaphthalenols, as well as methods of use for Compound 6 or its salt.

SUMMARY

Provided herein are compounds having a formula:

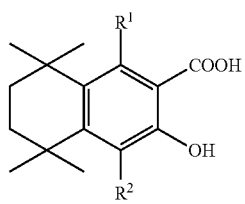

or a salt thereof.
Also provided herein are compounds having a formula:

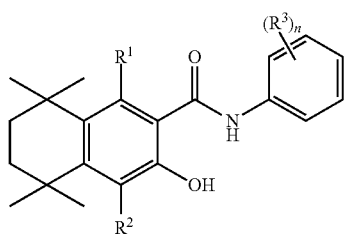

or a salt thereof.
Also provided herein are methods of preparing

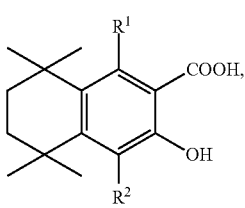

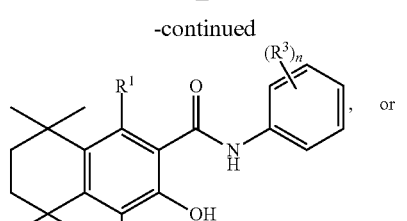

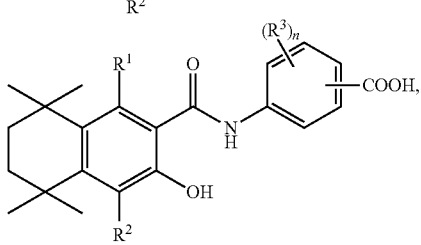

or a salt thereof.

DETAILED DESCRIPTION

Figure 1:
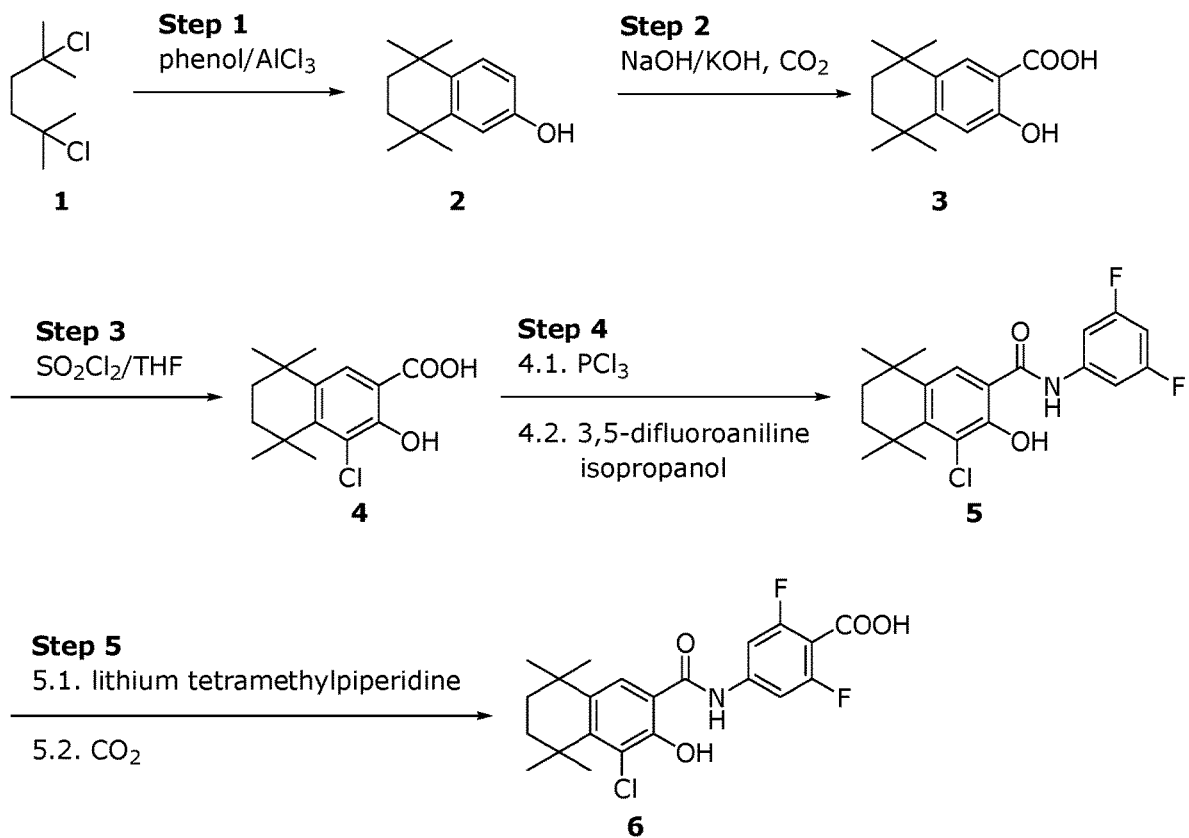
FIG. 1 shows an example of a synthetic scheme useful in preparing tetrahydronaphthalenols as described herein.

Certain tetrahydronaphthalenols have been prepared, for example as described in U.S. Pat. Nos. 6,387,950, 5,965,606, and 5,856,490, the content of each of which is incorporated herein by reference. However, improved methods of preparing tetrahydronaphthalenols are needed to provide the compounds described herein at commercial scale.

Definitions

The articles "a" and "an" refer to one or to more than one of the grammatical object of the article.

Numerical values relating to measurements are subject to measurement errors that place limits on their accuracy. For this reason, all numerical values provided herein, unless otherwise indicated, are to be understood as being modified by the term "about." Accordingly, the last decimal place of a numerical value provided herein indicates its degree of accuracy. Where no other error margins are given, the maximum margin is ascertained by applying the rounding-off convention to the last decimal place or last significant digit when a decimal is not present in the given numerical value.

The term "amelioration" means a lessening of severity of at least one indicator of a condition or disease, such as a delay or slowing in the progression of one or more indicators of a condition or disease. The severity of indicators may be determined by subjective or objective measures which are known to those skilled in the art.

The terms "composition" and "pharmaceutical composition" refer to a mixture of at least one compound described herein with a pharmaceutically acceptable carrier. The pharmaceutical composition facilitates administration of the compound to a patient or subject. Multiple techniques of administering a compound exist including, but not limited to, intravenous, oral, aerosol, parenteral, ophthalmic, nasal, pulmonary, and topical administration.

The terms "effective amount" and "therapeutically effective amount" refer to an amount of therapeutic compound, such as a compound described herein, administered to a subject, either as a single dose or as part of a series of doses, which is effective to produce a desired therapeutic effect. In general, the therapeutically effective amount can be estimated initially either in cell culture assays or in mammalian animal models, for example, in non-human primates, mice, rabbits, dogs, or pigs. The animal model may also be used to determine the appropriate concentration range and route of administration. Such information can then be used to determine useful doses and routes for administration in non-human subjects and human subjects.

The term "pharmaceutically acceptable carrier" means a pharmaceutically acceptable material, composition or carrier, such as a liquid filler, solid filler, stabilizer, dispersing agent, suspending agent, diluent, excipient, thickening agent, solvent, or encapsulating material, involved in carrying or transporting at least one compound described herein within or to the patient such that the compound may perform its intended function. A given carrier must be "acceptable" in the sense of being compatible with the other ingredients of a particular formulation, including the compounds described herein, and not injurious to the patient. Other ingredients that may be included in the pharmaceutical compositions described herein are known in the art and described, for example, in "Remington's Pharmaceutical Sciences" (Genaro (Ed.), Mack Publishing Co., 1985), the entire content of which is incorporated herein by reference.

The term "refractory disease" refers to a disease that continues to progress during treatment with a pharmaceutical ingredient other than the compounds provided herein, partially responds to the other treatment, or transiently responds to the other treatment. The term may be applied to each of the diseases referred to herein.

The term "salt" or "pharmaceutically acceptable salt" refers to derivatives of the disclosed compounds wherein the parent compound is modified by converting an existing acid or base moiety to its salt form. Salts, including pharmaceutically acceptable salts, can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two solvents. Lists of suitable salts are found in "Handbook of Pharmaceutical Salts: Properties, Selection, and Use" (P. Henrich Stahl & Camille G. Wermuth (Eds.), VHCA & Wiley-VCH, 2002), the entire content of which is incorporated herein by reference.

The terms "treatment" or "treating" refer to the application of one or more specific procedures used for the amelioration of a disease. A "prophylactic" treatment, refers to reducing the rate of progression of the disease or condition being treated, delaying the onset of that disease or condition, or reducing the severity of its onset.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the described subject matter and does not pose a limitation on the scope of the subject matter otherwise claimed. No language in the specification should be construed as indicating any non-claimed element essential to practicing the described subject matter.

Groupings of alternative elements or embodiments of this disclosure are not to be construed as limitations. Each group member may be referred to and claimed individually or in any combination with other members of the group or other elements found herein. Furthermore, a recited member of a group may be included in, or excluded from, another recited group for reasons of convenience or patentability. When any such inclusion or exclusion occurs, the specification is deemed to contain the group as modified thus fulfilling the written description of all Markush groups used in the appended claims.

References have been made to patents and printed publications throughout this specification, each of which are individually incorporated herein by reference in their entirety.

It is to be understood that the embodiments of this disclosure are illustrative. Accordingly, the present disclosure is not limited to that precisely as shown and described.

Compounds and Methods of Synthesis

Provided herein are methods of preparing tetrahydronaphthalenols and intermediate compounds useful in such methods.

Thus, in some embodiments, provided herein are intermediate compounds that may be useful in preparing tetrahydronaphthalenols, including Compound 6. The intermediate compounds include Compound 4 and Compound 5, or salts thereof. The intermediate compounds may be prepared as described herein, for example as shown in FIG. 1.

In some embodiments, provided herein are compounds having a formula:

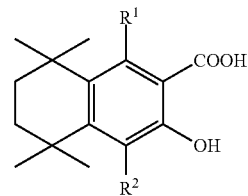

or a salt thereof,
wherein
$R^1$ is H, F, Cl, or Br;
$R^2$ is H, F, Cl, or Br; and
at least one of $R^1$ or $R^2$ is F, Cl, or Br.

In some embodiments, provided herein are compounds having a formula:

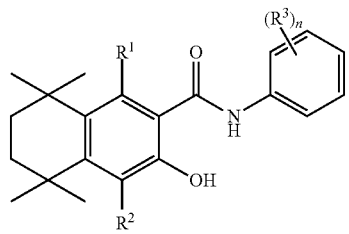

or a salt thereof, wherein
R¹ is H, F, Cl, or Br;
R² is H, F, Cl, or Br;
at least one of R¹ or R² is F, Cl, or Br;
each R³ is, independently, F, Cl, or Br; and
n is 0, 1, 2, 3, or 4.

In some embodiments, provided herein are compounds having a formula:

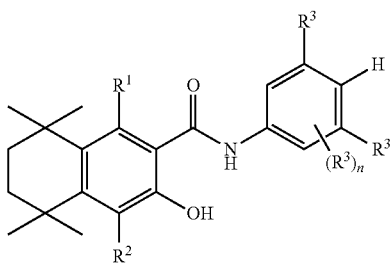

or a salt thereof,
wherein
R¹ is H, F, Cl, or Br;
R² is H, F, Cl, or Br;
at least one of R¹ or R² is F, Cl, or Br;
each R³ is, independently, F, Cl, or Br; and
n is 0, 1, or 2.

In some embodiments, provided herein are methods of preparing

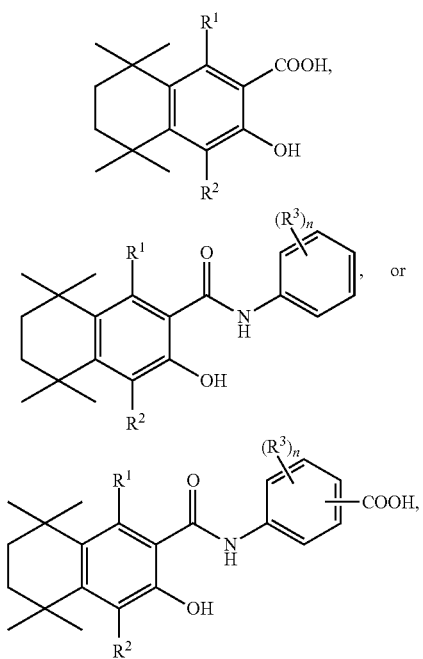

or a salt thereof,
wherein
R¹ is H, F, Cl, or Br;
R² is H, F, Cl, or Br;
at least one of R¹ or R² is F, Cl, or Br;
each R³ is, independently, F, Cl, or Br; and
n is 0, 1, 2, 3, or 4.

In some embodiments, provided herein are methods of preparing

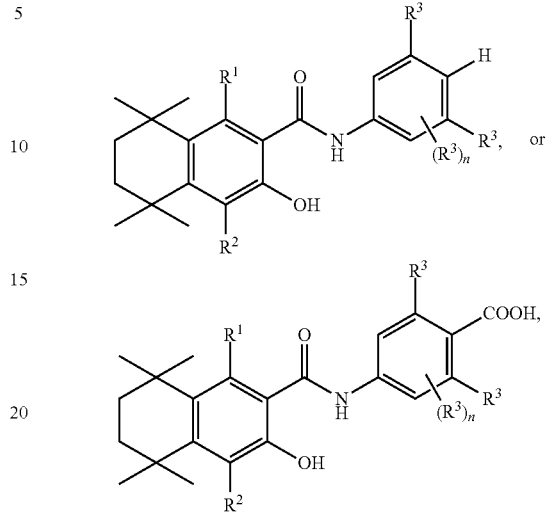

or a salt thereof,
wherein
R¹ is H, F, Cl, or Br;
R² is H, F, Cl, or Br;
at least one of R¹ or R² is F, Cl, or Br;
each R³ is, independently, F, Cl, or Br; and
n is 0, 1, or 2.

In some embodiments of the formulae provided herein, R¹ is H, and R² is F, Cl, or Br. In some embodiments, R¹ is H, and R² is F. In some embodiments, n is 2. In some embodiments, n is 0. In some embodiments, each R³ is F, and n is 2. In some embodiments, R¹ is H, R² is F, Cl, or Br, and n is 2. In some embodiments, at least one occurrence of R¹, R², or R³ is F. In some embodiments, each of R¹, R², and R³ is H or F, wherein at least one of R¹, R², or R³ is F. In some embodiments, n is 2, 3, or 4, and each R³, independently, includes F at each meta position (i.e., positions 3 and 5).

In some embodiments, provided herein are compounds having a formula:

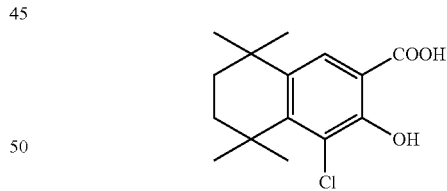

or a salt thereof.

In some embodiments, provided herein are compounds having a formula:

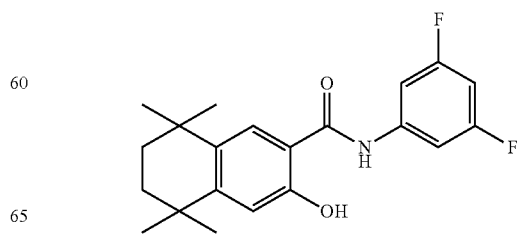

or a salt thereof.

In some embodiments, provided herein are compounds having a formula:

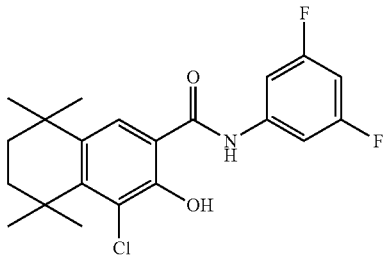 [SMILES: CC1(C)CCC(C)(C)c2c1cc(C(=O)Nc1cc(F)cc(F)c1)c(O)c2Cl]

or a salt thereof.

In some embodiments, provided herein are methods of preparing

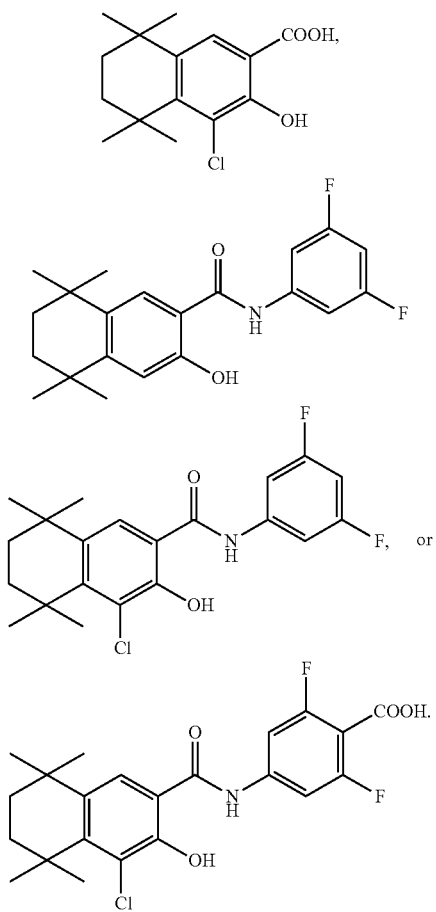

The synthetic steps described herein may be performed, independently, in the presence of one or more solvents suitable for the particular chemical reaction required of the synthesis. In some embodiments, the solvent is an anhydrous solvent, or the reaction is performed under anhydrous conditions.

The compounds described herein are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compound as described herein are modified by the use of appropriate reagents and conditions, for the introduction of the various moieties found in the formula as provided herein. Compounds described herein are synthesized using any suitable procedures starting from compounds that are available from commercial sources, or are prepared using procedures described herein.

Compounds described herein also include isotopically-labeled compounds wherein one or more atoms is replaced by an atom having the same atomic number, but an atomic mass or mass number different from the atomic mass or mass number predominantly found in nature. Examples of isotopes suitable for inclusion in the compounds described herein include and are not limited to $^{2}$H, $^{3}$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In some embodiments, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In some embodiments, the compounds described herein are labeled by other means, including, but not limited to, the use of chromophores or fluorescent moieties, bioluminescent labels, or chemiluminescent labels.

In some embodiments, the solid forms (e.g., precipitated or crystalline forms) provided herein are prepared as particles or as a compressed solid. In some embodiments, these solid forms are coated. In some embodiments, the particles comprise a mean particle size of about 10 microns or less. In some embodiments, the particles comprise a mean particle size of about 2 microns or less. In some embodiments, the particles comprise a mean particle size of about 10-20 microns or more. In some embodiments, the solid forms or particles provided herein are formulated as a suspension in liquid or as a dry powder for aerosol administration.

In some embodiments, the solid form is about, or at least about, 75, 80, 85, 90, 95, or 100% by mass of the particle.

In some embodiments, the particle comprises a particle surface wherein the particle surface comprises a coating on at least a portion of the particle surface. In some embodiments, the coating comprises a film coating. In some embodiments, the particle comprises a film coating with a polymer or co-polymer to form microcapsules, which may be used to form chewable taste-masked granules. In some embodiments, the coating comprises a polymer or co-polymer. In some embodiments, the coating comprises one or more of cellulose acetate phthalate, cellulose acetate trimellate, ethyl cellulose, glycol, hydroxy propyl cellulose, hydroxy propyl methyl cellulose, hydroxy propyl methyl cellulose phthalate, methacrylic acid co-polymer, high molecular weight polyethylene, polyvinyl alcohol, polyvinyl pyrrolidone, starch, or shellac. In some embodiments, the coating comprises a sugar. In some embodiments, the coating comprises a sugar coating. In some embodiments, the particles described herein are sugar coated. In some embodiments, the particles described herein are not sugar coated. In some embodiments, the coating comprises an enteric coating. In some embodiments, the coating is an extended release coating. In some embodiments, the coating is a sustained release coating. In some embodiments, the coating comprises a controlled release coating. In some embodiments, the coating is a delayed release coating. In some embodiments, the particles described herein may include a second coating layered atop a first coating. In some embodiments, the coating is stable below about pH 7. In some embodiments, the coating is stable below about pH 5.5. In some embodiments, the coating is stable in an acidic environment. In some embodiments, the coating is stable in gastric fluid and unstable in intestinal fluid.

In some embodiments, a dosage form comprising a plurality of particles comprises coated particles wherein the coating is selected, independently for each particle, from a coating described herein. Accordingly, in some embodiments a plurality of particles may include a mixture of enteric coated particles and extended release coated particles.

In some embodiments, the particles described herein are encapsulated within a coating.

In some embodiments of the particles described herein, the coating is 25% or less by mass of the coated particle.

In some embodiments, the particles described herein are provided as a composition, comprising a plurality of particles, which may include one or more carriers. In some embodiments, the plurality of particles is encapsulated in a capsule, a compression coating, a film coating, or a powder coating. In some embodiments, the particles or plurality of particles, whether as a powder, compressed powder, or tablet, are spray coated. In some embodiments, the plurality of particles is a loose powder within an ingestible capsule. In some embodiments, the plurality of particles is compressed into a friable solid.

In some embodiments, provided herein are dosage forms, comprising a particle, a composition, or a pharmaceutical composition described herein. In some embodiments, the dosage form comprises a plurality of the particles as a powder or as a compressed powder. In some embodiments, the dosage form comprises a plurality of the particles in a liquid suspension. As described above, the particles may be coated.

In some embodiments, the solid forms, particles, compositions, or pharmaceutical compositions described herein are housed in at least one container.

Compounds described herein are synthesized using any suitable procedures starting from compounds that are available from commercial sources, or are prepared using procedures described herein.

Figure 2:
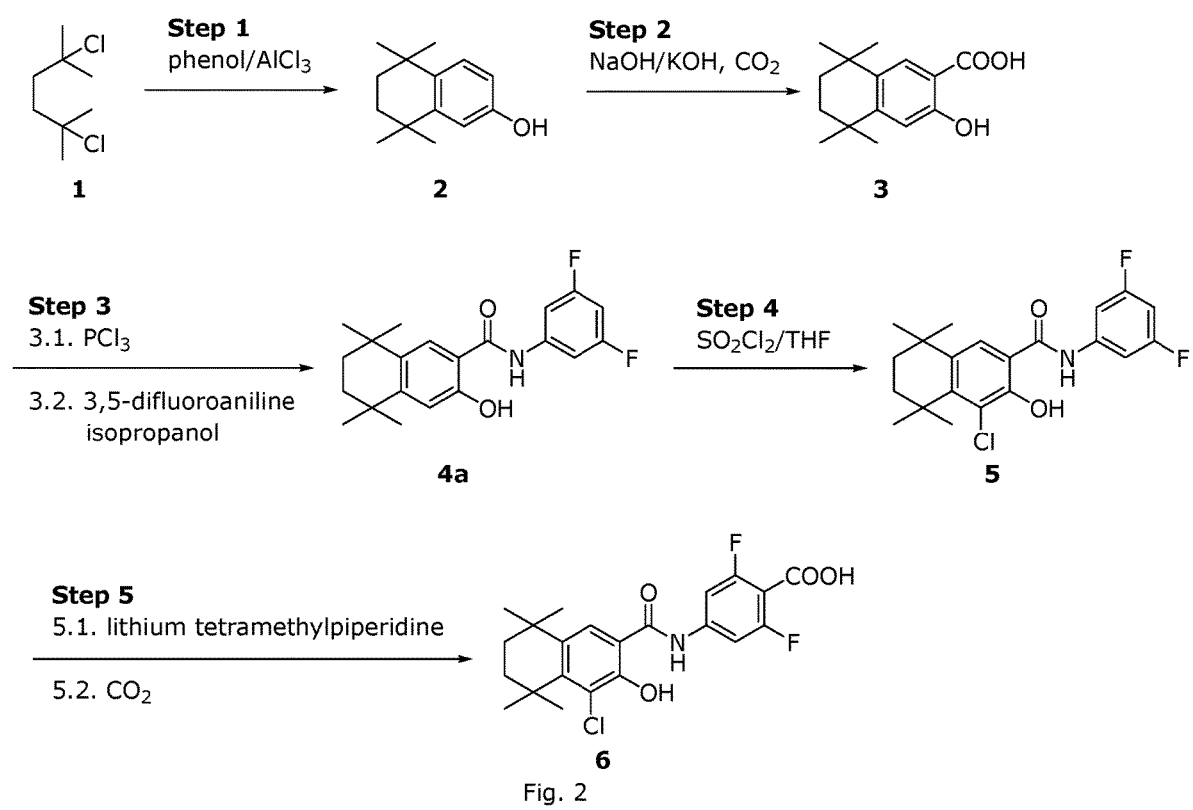
FIG. 2 shows another example of a synthetic scheme useful in preparing tetrahydronaphthalenols as described herein.

In some embodiments, the compounds described herein may be prepared by a method of synthesis that comprises any one or more of the synthetic schemes shown in the Examples, in FIG. 1, or in FIG. 2.

In some embodiments, reactive functional groups, such as hydroxyl, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal. In some embodiments, protective groups are removed by acid, base, reducing conditions (for example, by hydrogenolysis), or oxidative conditions. Groups such as trityl, dimethoxytrityl, acetal, and t-butyldimethylsilyl are acid labile.

In some embodiments, the compounds provided herein are provided as a salt. In some embodiments, the salt form is a pharmaceutically acceptable salt of the compound.

Compositions

In some embodiments, provided herein are compositions, comprising a compound described herein.

In some embodiments, provided herein are pharmaceutical compositions, comprising a compound described herein and a pharmaceutically acceptable carrier.

Methods of Treatment

Compound 6, is a selective retinoid acid receptor alpha (RARα) agonist, is orally bioavailable, and has potential antineoplastic activity. Compound 6 has no observable activity against RARβ/γ. Without wishing to be bound by theory, upon administration, RARα agonist Compound 6 binds to and activates RARα, which promotes RARα-mediated signaling. This results in the transcription of RARα-responsive genes, which are responsible for cellular differentiation and proliferation. This results in the induction of cellular differentiation and apoptosis, and leads to the inhibition of cellular proliferation and tumorigenesis. RARα is a nuclear receptor and a member of the steroid receptor superfamily. Modulated RARα signaling is correlated with cancer development in a variety of cancer cell types, including lymphomas or blood cancers, such as multiple myeloma or a leukemia.

In some embodiments, provided herein are methods of treating a disease in a subject in need thereof, comprising administering to the subject a therapeutically effective amount of a compound described herein (e.g. a form of Compound 6, or its salt). In some embodiments, provided herein are methods of modulating RARα in a subject in need thereof, comprising administering to the subject a therapeutically effective amount of a compound described herein (e.g. a form of Compound 6, or its salt). In some embodiments, the modulation is activation of RARα. In some embodiments, provided herein are methods of modulating gene expression, comprising administering to the subject a therapeutically effective amount of a compound described herein (e.g. a form of Compound 6, or its salt).

In some embodiments, the disease is related to one or more cellular processes, including cellular proliferation or the immune response. In some embodiments of the methods provided herein, the disease is selected from a cellular proliferation disorder (e.g. cancer or tumor), or an autoimmune disorder. In some embodiments, the cancer is a non-solid cancer (e.g., a liquid cancer, e.g., a blood cancer). In some embodiments, the cancer or tumor is a solid cancer or tumor.

In some embodiments, the subject comprises a refractory disease. In some embodiments, the refractory disease comprises a refractory cellular proliferation disorder, e.g., cancer or tumor, or a refractory autoimmune disorder.

In certain embodiments of methods for treating an autoimmune disorder, the methods treat an autoimmune disease selected from the group consisting of acute disseminated encephalomyelitis (ADEM), Addison's disease, an allergy, allergic rhinitis, anti-phospholipid antibody syndrome (APS), an arthritis, asthma, acquired immunodeficiency syndrome (AIDS), autoimmune hemolytic anemia, autoimmune hepatitis, autoimmune inner ear disease, bullous pemphigoid, celiac disease, Chagas disease, chronic obstructive pulmonary disease (COPD), diabetes mellitus type 1 (IDDM), endometriosis, a gastrointestinal disorder, a glomerulonephritis, Goodpasture's syndrome, Graves' disease, Guillain-Barré syndrome (GBS), Hashimoto's thyroiditis, hidradenitis suppurativa, idiopathic thrombocytopenic purpura, interstitial nephritis, interstitial cystitis, a lupus, morphea, multiple sclerosis (MS), myasthenia gravis, a myopathy, myositis, narcolepsy, neuromyotonia, pemphigus vulgaris, pernicious anaemia, primary biliary cirrhosis, psoriasis, psoriatic arthritis, a pulmonary fibrosis, recurrent disseminated encephalomyelitis, rheumatic fever, schizophrenia, scleroderma, Sjögren's syndrome, a skin disorder, tenosynovitis, uveitis, a vasculitis, or vitiligo.

In certain embodiments, the disease does not include multiple sclerosis, i.e. the subject receiving treatment does not have, or has not been diagnosed with, multiple sclerosis.

In certain embodiments, the arthritis is monoarthritis, oligoarthritis, polyarthritis, osteoarthritis, rheumatoid arthritis, juvenile idiopathic arthritis, septic arthritis, spondyloarthropathy, gout, pseudogout, or Still's disease.

In some embodiments, the gastrointestinal disorder is an irritable bowel disease or an inflammatory bowel disease. In other embodiments, the inflammatory bowel disease is Crohn's disease or ulcerative colitis.

In some embodiments, the lupus is discoid lupus erythematosus, drug-induced lupus erythematosus, lupus nephritis, neonatal lupus, subacute cutaneous lupus erythematosus, or systemic lupus erythematosus.

In some embodiments, the autoimmune disorder is a myopathy with an autoimmune component such as dermatomyositis, inclusion body myositis, or polymyositis.

In some embodiments, the skin disorder is dermatitis, eczema, statis dermatitis, hidradenitis suppurativa, psoriasis, rosacea, or scleroderma.

In some embodiments, the vasculitis is Buerger's disease, cerebral vasculitis, Churg-Strauss arteritis, cryoglobulinemia, essential cryoglobulinemic vasculitis, giant cell arteritis, Golfer's vasculitis, Henoch-Schonlein purpura, hypersensitivity vasculitis, Kawasaki disease, microscopic polyarteritis/polyangiitis, polyarteritis nodosa, polymyalgia rheumatica (PMR), rheumatoid vasculitis, Takayasu arteritis, or Wegener's granulomatosis.

In some embodiments, the autoimmune disease is multiple sclerosis, psoriasis, rheumatoid arthritis, glomerulonephritis, pulmonary fibrosis, interstitial nephritis, or an inflammatory bowel disease.

While the methods as described refer to the compounds described herein, it is to be understood that the compounds may be used in conjunction with these methods in the form of a composition or a pharmaceutical composition as well.

Actual dosage levels of the active ingredients (e.g. the compounds of the formulae provided herein), the compositions, or the pharmaceutical compositions provided herein may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health, and prior medical history of the patient being treated, and like factors well-known in the medical arts. A medical doctor, e.g., physician or veterinarian, having ordinary skill in the art may readily determine and prescribe the effective amount of the pharmaceutical composition required. For example, the physician or veterinarian could start doses of the compounds employed in the pharmaceutical composition at levels lower than that required in order to achieve the desired therapeutic effect and gradually increase the dosage until the desired effect is achieved.

Administration of a compound, a composition, or a combination disclosed herein includes a variety of enteral or parenteral approaches selected from, without limitation: oral administration in any acceptable form, such as, e.g., tablet, liquid, capsule, powder, or the like; topical administration in any acceptable form, such as, e.g., drops, spray, creams, gels or ointments; buccal, nasal, and/or inhalation administration in any acceptable form; rectal administration in any acceptable form; vaginal administration in any acceptable form; intravascular administration in any acceptable form, such as, e.g., intravenous bolus injection, intravenous infusion, intra-arterial bolus injection, intra-arterial infusion and catheter instillation into the vasculature; peri- and intra-tissue administration in any acceptable form, such as, e.g., intraperitoneal injection, intramuscular injection, subcutaneous injection, subcutaneous infusion, intraocular injection, retinal injection, or sub-retinal injection or epidural injection; intravesicular administration in any acceptable form, such as, e.g., catheter instillation; and by placement device, such as, e.g., an implant, a stent, a patch, a pellet, a catheter, an osmotic pump, a suppository, a bioerodible delivery system, a non-bioerodible delivery system or another implanted extended or slow release system.

A compound, a composition, or a combination disclosed herein can be administered to a mammal using a variety of routes. Routes of administration of include, without limitation, oral, nasal, rectal, intravaginal, parenteral, buccal, sublingual, or topical. In some embodiments, the oral or nasal route of administration is an oral inhalational or nasal inhalational route of administration. The compounds for use as described herein may be formulated for administration by any suitable route to achieve the particular method being applied. In some embodiments, routes of administration suitable for treating an RARα-related disease as disclosed herein include both local and systemic administration. Local administration results in significantly more delivery of a compound, a composition, or a combination to a specific location as compared to the entire body of the mammal, whereas, systemic administration results in delivery of a compound, a composition, or a combination to essentially the entire body of the individual. Routes of administration suitable for treating an RARα-related disease as disclosed herein also include both central and peripheral administration. Central administration results in delivery of a compound, a composition, or a combination to essentially the central nervous system of the individual and includes, e.g., nasal administration, intrathecal administration, epidural administration as well as a cranial injection or implant. In some embodiments, central administration is used to administer the compound, composition, or combinations described herein.

Central administration by the nasal route, which targets drug absorption through the vascular plexus of the nasal cavity, is distinct from administration by nasal inhalation, which delivers drug through the pulmonary system. Whereas the latter typically uses liquid or dry powder aerosols with mean particle sizes less than 10 microns, and in some embodiments around 2 microns or less, central administration is typically accomplished using mean particle sizes of 10-20 microns or larger. Mists and aerosols can be generated using nebulizers, dry powder inhalers, pressurized aerosols, and atomization pumps, the latter being preferred. It is also feasible to use nose drops for central administration by the nasal route.

Peripheral administration results in delivery of a compound, a composition, or a combination to essentially any area of an individual outside of the central nervous system and encompasses any route of administration other than direct administration to the spine or brain. The actual route of administration of a compound, a composition, or a combination disclosed herein used can be determined by a person of ordinary skill in the art by taking into account factors, including, without limitation, the type of an RARα-related disease, the location of the an RARα-related disease, the cause of the an RARα-related disease, the severity of the an RARα-related disease, the duration of treatment desired, the degree of relief desired, the duration of relief desired, the particular compound, composition, or combination, the rate of excretion of the compound, composition, or combination used, the pharmacodynamics of the compound, composition, or combination used, the nature of the other compounds to be included in the composition or combination, the particular route of administration, the particular characteristics, history and risk factors of the individual, such as, e.g., age, weight, general health and the like, the response of the individual to the treatment, or any combination thereof. An effective dosage amount of a compound, a composition, or a combination disclosed herein can thus readily be determined by the person of ordinary skill in the art considering all criteria and utilizing their best judgment on the individual's behalf.

In some embodiments, the compounds having the formula

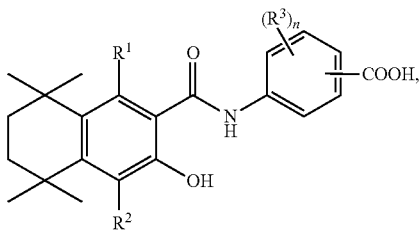

or a salt thereof,

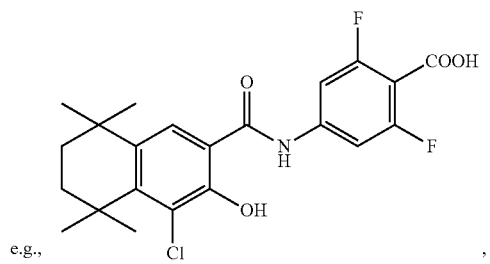 [SMILES: CC1(C)CCC(C)(C)c2c1cc(C(=O)Nc1cc(F)c(C(=O)O)c(F)c1)c(O)c2Cl]

e.g., or a salt thereof,
which are prepared as described herein, are useful in methods of treatment for RARα-related diseases, including those diseases benefiting from therapeutic RARα-modulation (e.g., RARα-activation) or antineoplastic activity.

While the methods as described refer to the compounds described herein, it is to be understood that the compounds may be used in conjunction with these methods in the form of a composition or a pharmaceutical composition as well.

Actual dosage levels of the active ingredients (e.g. the compounds of the formulae provided herein), the compositions, or the pharmaceutical compositions provided herein may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health, and prior medical history of the patient being treated, and like factors well-known in the medical arts. A medical doctor, e.g., physician or veterinarian, having ordinary skill in the art may readily determine and prescribe the effective amount of the pharmaceutical composition required. For example, the physician or veterinarian could start doses of the compounds employed in the pharmaceutical composition at levels lower than that required in order to achieve the desired therapeutic effect and gradually increase the dosage until the desired effect is achieved.

Kits

In some embodiments, provided herein are packaged compounds, packaged compositions, or packaged pharmaceutical compositions, comprising a container holding a therapeutically effective amount of a compound described herein, and instructions for using the compound in accordance with one or more of the methods provided herein.

The present compounds and associated materials can be finished as a commercial product by the usual steps performed in the present field, for example by appropriate sterilization and packaging steps. For example, the material can be treated by UV/vis irradiation (200-500 nm), for example using photo-initiators with different absorption wavelengths (e.g. Irgacure 184, 2959), preferably water-soluble initiators (e.g. Irgacure 2959). Such irradiation is usually performed for an irradiation time of 1-60 min, but longer irradiation times may be applied, depending on the specific method. The material according to the present disclosure can be finally sterile-wrapped so as to retain sterility until use and packaged (e.g. by the addition of specific product information leaflets) into suitable containers (boxes, etc.).

According to further embodiments, the present compounds can also be provided in kit form combined with other components necessary for administration of the material to the patient. For example, disclosed kits, such as for use in the treatment of an autoimmune or a cellular proliferation disorder, can further comprise, for example, administration materials.

The kits are designed in various forms based on the specific deficiencies they are designed to treat.

The compounds or compositions provided herein may be prepared and placed in a container for storage at ambient or elevated temperature. When the compound or composition is stored in a polyolefin plastic container as compared to a polyvinyl chloride plastic container, discoloration of the compound or composition may be reduced, whether dissolved or suspended in a liquid composition (e.g., an aqueous or organic liquid solution), or as a solid. Without wishing to be bound by theory, the container may reduce exposure of the container's contents to electromagnetic radiation, whether visible light (e.g., having a wavelength of about 380-780 nm) or ultraviolet (UV) light (e.g., having a wavelength of about 190-320 nm (UV B light) or about 320-380 nm (UV A light)). Some containers also include the capacity to reduce exposure of the container's contents to infrared light, or a second component with such a capacity. The containers that may be used include those made from a polyolefin such as polyethylene, polypropylene, polyethylene terephthalate, polycarbonate, polymethylpentene, polybutene, or a combination thereof, especially polyethylene, polypropylene, or a combination thereof. In some embodiments, the container is a glass container. The container may further be disposed within a second container, for example, a paper, cardboard, paperboard, metallic film, or foil, or a combination thereof, container to further reduce exposure of the container's contents to UV, visible, or infrared light. Compounds and compositions benefiting from reduced discoloration, decomposition, or both during storage, include eye drop solutions or implants that include a compound or composition thereof provided herein. The compounds or compositions provided herein may need storage lasting up to, or longer than, three months; in some cases up to, or longer than one year. The containers may be in any form suitable to contain the contents; for example, a bag, a bottle, or a box. In some embodiments, the container is one that includes a reduced capacity to adsorb the compound or composition provided herein to a surface of the container and thereby prevent the apparent reduction in concentration of the compound or composition disposed within the container.

The following examples further illustrate aspects of the present disclosure. However, they are in no way a limitation of the teachings or disclosure as described herein.

EXAMPLES

Example 1—Preparation of Compound 6: 4-(4-chloro-3-hydroxy-5,5,8,8-tetramethyl-acid Compound 6 may be prepared as shown in FIG. 1 starting from commercially available Compound 1 (2,5-dichloro-2,5-dimethylhexane), or generally as described below in steps 2-5 starting from commercially available Compound 2 (5,5,8,8-tetramethyl-5,6,7,8-tetrahydronaphthalen-2-ol).

Step 2—Synthesis of Compound 3: 3-hydroxy-5,5,8,8-tetramethyl-5,6,7,8-tetrahydronaphthalene-2-carboxylic acid. A pressure reaction vessel is charged with 100 g of sodium 5,5,8,8-tetramethyl-5,6,7,8-tetrahydronaphthalen-2-olate (Na·Compound 2) and g of 5,6,7,8-tetrahydro-5,5,8,8-tetramethyl-β-naphthol in a high boiling solvent at 170° C. and at a carbon dioxide pressure of 10 kg/cm$^2$ (G) for 2 hours with stirring. The reaction mixture is cooled and charged with 500 mL of water, followed by separation into the reaction medium layer and water layer at 90° C. The water layer is extracted with 50 mL of xylene. The water layer is made acidic with dilute sulfuric acid, and compound 3 is isolated.

Step 3—Synthesis of Compound 4: 4-chloro-3-hydroxy-5,5,8,8-tetramethyl-5,6,7,8-tetrahydronaphthalene-2-carboxylic acid. Sulfuryl chloride (12.7 kg, 1 eq.) is added portion-wise to a solution of Compound 3 (23.0 kg, 1 eq.) in tetrahydrofuran, then the mixture is heated and agitated until the reaction is complete. The mixture is cooled, then ethyl acetate is added. The mixture is washed with brine, then the organics are concentrated and co-evaporated with heptane. Heptane is added and the slurry is cooled, then the product is collected by filtration, rinsing forward with heptane. The product, Compound 4, is dried (17.7-23.8 kg, 67-91% yield).

Step 4—Synthesis of Compound 5. Phosphorus trichloride (4.2 kg, 1.44 eq.) is added to a suspension of Compound 4 (18 kg, 1.0 eq.) in toluene, then the mixture is heated and agitated until solution is achieved. A solution of 3,5-difluoroaniline (9 kg, 1.09 eq.) in toluene is then added and heating is continued until the reaction is complete. The mixture is cooled slightly, then partially concentrated and co-evaporated with isopropanol. Further isopropanol is added, then the slurry is heated to dissolve the product and again is partially concentrated. The resulting slurry is cooled, then the product is collected by filtration. The filtrate is partially concentrated, then cooled to precipitate a second crop which is collected by filtration. Both crops are then dried under vacuum at <60° C. to give Compound 5 (18.1-20.1 kg, 72-80% yield).

Step 5—Synthesis of Compound 6. A mixture of Compound 5 (15 kg, 1 eq.) and 2,2,6,6-tetramethylpiperidine (10.7 kg, 2 eq.) in tetrahydrofuran is cooled. N-Hexyllithium (43.1 kg 2.5 M in hexane, 4 eq.) is added to the mixture slowly while maintaining the temperature, then the mixture is agitated for a specified time period. The mixture is quenched over dry ice (about 186 kg), then heated and agitated until all of the solid dry ice has disappeared. Water is added, then the layers are separated and a second extraction of the organics is performed with water. The aqueous layers are combined and acidified with hydrochloric acid (15.01 kg, 4 eq.) then extracted twice with ethyl acetate. The combined organics are concentrated and co-evaporated with toluene. Further toluene is added, then the mixture is cooled. The resulting slurry is filtered, rinsing forward with cold toluene. The product, Compound 6, is dried (40-50° C.) then stored in the dark and refrigerated (11.7-15.9 kg, 70-95% yield). $^1$HNMR (CD$_3$OD): d 1.34 (s, 6H), 1.54 (s, 6H), 1.68 (m, 2H), 1.75 (m, 2H), 7.53 (d, J$_{HF}$=10.2 Hz, 2H).

EMBODIMENTS

Embodiment 1 A compound, having a formula:

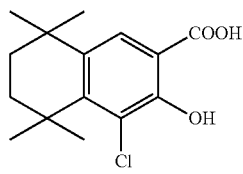 [SMILES: CC1(C)CCC(C)(C)c2c1cc(C(=O)O)c(O)c2Cl]

or a salt thereof.

Embodiment 2. A method of preparing the compound of Embodiment 1, comprising contacting

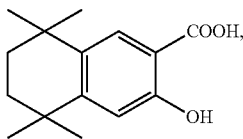 [SMILES: CC1(C)CCC(C)(C)c2cc(C(=O)O)c(O)cc21]

with sulfuryl chloride to form the compound.

Embodiment 3. A compound, having a formula:

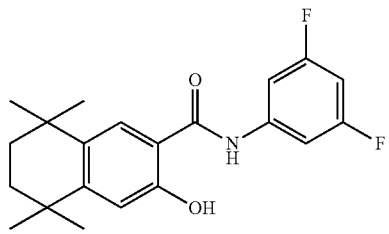 [SMILES: CC1(C)CCC(C)(C)c2cc(C(=O)Nc3cc(F)cc(F)c3)c(O)cc21]

or a salt thereof.

4. A method of preparing the compound of Embodiment 3, comprising

A) contacting

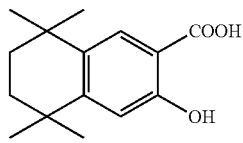 [SMILES: CC1(C)CCC(C)(C)c2cc(C(=O)O)c(O)cc21]

with phosphorous trichloride to form an intermediate; and

B) contacting the intermediate with 3,5-difluoroaniline to form the compound.

Embodiment 5. A compound, having a formula:

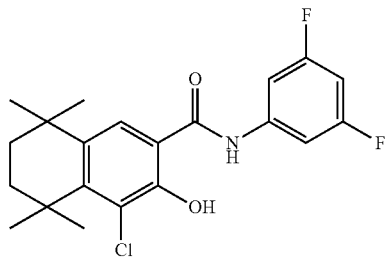 [SMILES: CC1(C)CCC(C)(C)c2c1cc(C(=O)Nc1cc(F)cc(F)c1)c(O)c2Cl]

or a salt thereof.

Embodiment 6. A method of preparing the compound of Embodiment 5, comprising

A) contacting

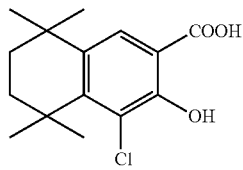 [SMILES: CC1(C)CCC(C)(C)c2c1cc(C(=O)O)c(O)c2Cl]

with phosphorous trichloride to form an intermediate; and

B) contacting the intermediate with 3,5-difluoroaniline to form the compound.

Embodiment 7. A method of preparing the compound of Embodiment 5, comprising contacting

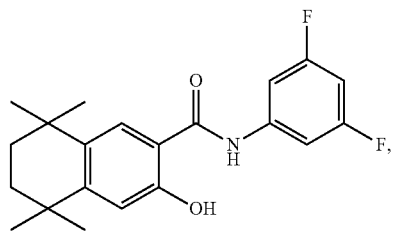 [SMILES: CC1(C)CCC(C)(C)c2cc(C(=O)Nc3cc(F)cc(F)c3)c(O)cc21]

with sulfuryl chloride to form the compound.

Embodiment 8. A method of preparing a compound having a formula:

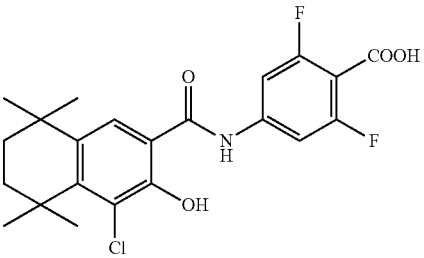 [SMILES: CC1(C)CCC(C)(C)c2c1cc(C(=O)Nc1cc(F)c(C(=O)O)c(F)c1)c(O)c2Cl]

or a salt thereof,
comprising,
A) contacting the compound of Embodiment 5 with lithium tetramethylpiperidine to form an intermediate; and
B) contacting the intermediate with $CO_2$ to form the compound.

Embodiment 9. The method of any one of Embodiments 2, 4, 6, 7, or 8, wherein each contacting, independently, occurs in the presence of a solvent.

Embodiment 10. The compound of Embodiment 5, which is a solid form of

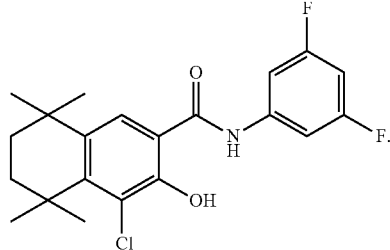

Embodiment 11. The compound of Embodiment 10, which is prepared by precipitation from a solvent comprising isopropanol.

Embodiment 12. The compound of Embodiment 5, which is a crystalline form of

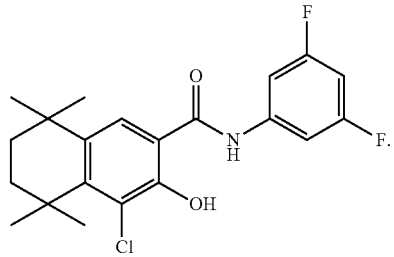 [SMILES: CC1(C)CCC(C)(C)c2c1cc(C(=O)Nc1cc(F)cc(F)c1)c(O)c2Cl]

Embodiment 13. The compound of Embodiment 12, which is prepared by crystallization from a solvent comprising isopropanol.

Embodiment 14. A solid form of

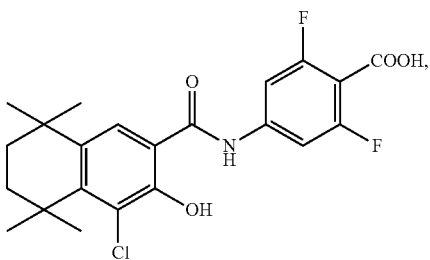 [SMILES: CC1(C)CCC(C)(C)c2c1cc(C(=O)Nc1cc(F)c(C(=O)O)c(F)c1)c(O)c2Cl]

which is prepared by precipitation from toluene.

Embodiment 15. A crystalline form of

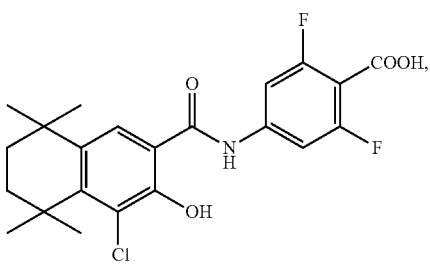 [SMILES: CC1(C)CCC(C)(C)c2c1cc(C(=O)Nc1cc(F)c(C(=O)O)c(F)c1)c(O)c2Cl]

which is prepared by crystallization from toluene.

Embodiment 16. The compound of Embodiment 3, which is a solid form of

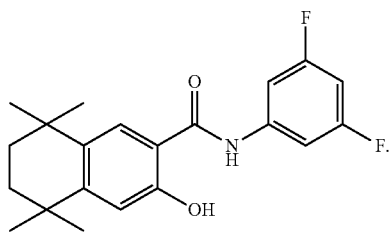 [SMILES: CC1(C)CCC(C)(C)c2cc(C(=O)Nc3cc(F)cc(F)c3)c(O)cc21]

Embodiment 17. A composition comprising the compound, solid form, or crystalline form of any one of Embodiments 1, 3, 5, or 10-16.

Embodiment 18. A particle, comprising the solid form of Embodiment 14 or the crystalline form of Embodiment 15, and a pharmaceutically acceptable carrier.

Embodiment 19. A pharmaceutical composition, comprising the solid form of Embodiment 14, the crystalline form of Embodiment 15, the particle of Embodiment 18, and a pharmaceutically acceptable carrier.

Embodiment 20. The pharmaceutical composition of Embodiment 19, wherein the compound is present in the pharmaceutical composition in an amount of at least about 80% by weight.

Embodiment 21. The pharmaceutical composition of Embodiments 19 or 20, formulated as an oral, parenteral, topical, or inhalational dosage form, or formulated for oral, parenteral, topical, or inhalational administration.

Embodiment 22. A method of treating a disease in a subject in need thereof, comprising administering to the subject an effective amount of:
the solid form of Embodiment 14;
the crystalline form of Embodiment 15;
the particle of Embodiment 18; or
the pharmaceutical composition of one of Embodiments 19-21.

Embodiment 23. The method of Embodiment 22, wherein the disease is a retinoic acid receptor alpha related disease.

Embodiment 24. The method of Embodiment 22, wherein the disease is an autoimmune disorder.

Embodiment 25. The method of Embodiment 22, wherein the disease is selected from a cellular proliferation disorder.

Embodiment 26. The method of Embodiment 22, wherein the disease is selected from a cancer or tumor.

Embodiment 27. A method of modulating retinoic acid receptor alpha in a subject in need thereof, comprising administering to the subject an effective amount of:
the solid form of Embodiment 14;
the crystalline form of Embodiment 15;
the particle of Embodiment 18; or
the pharmaceutical composition of one of Embodiments 19-21.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A compound, having a formula:

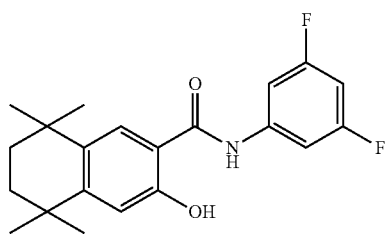 [SMILES: CC1(C)CCC(C)(C)c2cc(C(=O)Nc3cc(F)cc(F)c3)c(O)cc21]

or a salt thereof.

2. A method of preparing the compound of claim 1, comprising

A) contacting

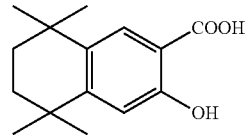 [SMILES: CC1(C)CCC(C)(C)c2cc(C(=O)O)c(O)cc21]

with phosphorous trichloride to form an intermediate; and

B) contacting the intermediate with 3,5-difluoroaniline to form the compound.

3. A compound, having a formula:

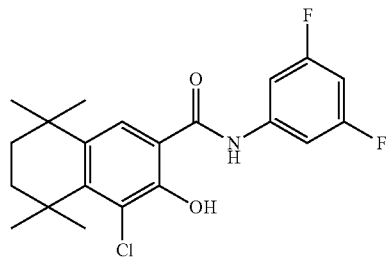 [SMILES: CC1(C)CCC(C)(C)c2c1cc(C(=O)Nc1cc(F)cc(F)c1)c(O)c2Cl]

or a salt thereof.

4. A method of preparing the compound of claim 3, comprising

A) contacting

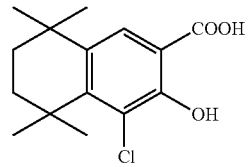 [SMILES: CC1(C)CCC(C)(C)c2c1cc(C(=O)O)c(O)c2Cl]

with phosphorous trichloride to form an intermediate; and

B) contacting the intermediate with 3,5-difluoroaniline to form the compound.

5. A method of preparing the compound of claim 3, comprising contacting

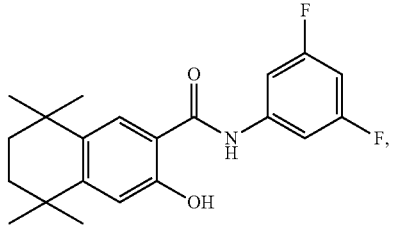 [SMILES: CC1(C)CCC(C)(C)c2cc(C(=O)Nc3cc(F)cc(F)c3)c(O)cc21]

with sulfuryl chloride to form the compound.

6. A method of preparing a compound having a formula:

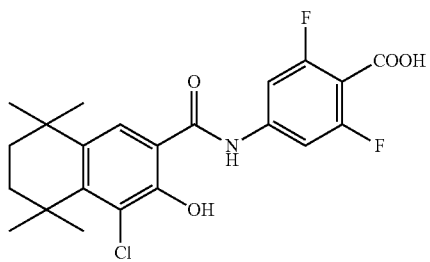 [SMILES: CC1(C)CCC(C)(C)c2c1cc(C(=O)Nc1cc(F)c(C(=O)O)c(F)c1)c(O)c2Cl]

or a salt thereof,
comprising,
  A) contacting the compound of claim 3 with lithium tetramethylpiperidine to form an intermediate; and
  B) contacting the intermediate with $CO_2$ to form the compound.

7. The compound of claim 3, which is a solid form of

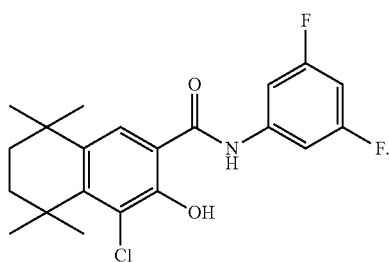

8. The compound of claim 7, which is prepared by precipitation from a solvent comprising isopropanol.

9. The compound of claim 3, which is a crystalline form of

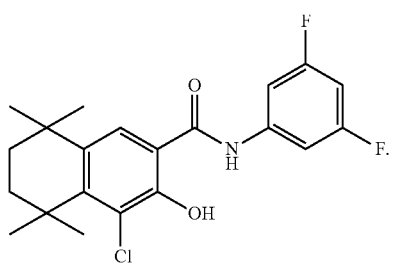

10. The compound of claim 9, which is prepared by crystallization from a solvent comprising isopropanol.

11. The method of claim 6, further comprising precipitating the compound of structure:

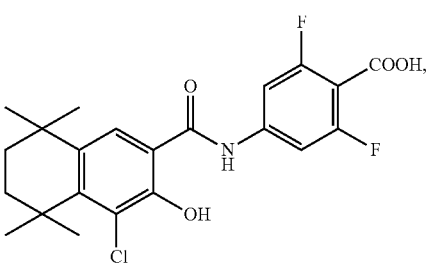 [SMILES: CC1(C)CCC(C)(C)c2c1cc(C(=O)Nc1cc(F)c(C(=O)O)c(F)c1)c(O)c2Cl]

from toluene, thereby obtaining a solid form of the compound.

12. The method of claim 11, wherein the solid form is a crystalline form.

13. The compound of claim 1, which is a solid form of

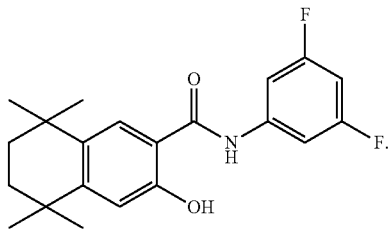 [SMILES: CC1(C)CCC(C)(C)c2cc(C(=O)Nc3cc(F)cc(F)c3)c(O)cc21]

14. A pharmaceutical composition, comprising the solid form of claim 13, and a pharmaceutically acceptable carrier.

15. The pharmaceutical composition of claim 14, wherein the compound is present in the pharmaceutical composition in an amount of at least about 80% by weight.

16. The pharmaceutical composition of claim 14, which is an oral, parenteral, topical, or inhalational dosage form.

17. A method of treating a retinoic acid receptor alpha related disease in a subject in need thereof, comprising administering to the subject an effective amount of a solid form of

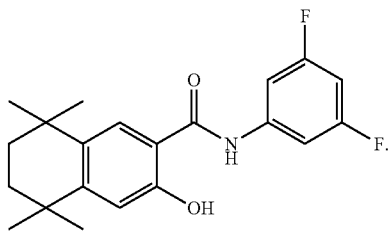 [SMILES: CC1(C)CCC(C)(C)c2cc(C(=O)Nc3cc(F)cc(F)c3)c(O)cc21]

* * * * *